US006297289B2

(12) United States Patent
Siff

(10) Patent No.: US 6,297,289 B2
(45) Date of Patent: Oct. 2, 2001

(54) PRODUCT FOR MOISTURIZING AN EYE

(75) Inventor: Elliott J. Siff, Westport, CT (US)

(73) Assignee: Belmar Corporation, Westport, CT (US)

( * ) Notice: Subject to any disclaimer, the term of this patent is extended or adjusted under 35 U.S.C. 154(b) by 0 days.

(21) Appl. No.: 09/849,367

(22) Filed: May 7, 2001

Related U.S. Application Data

(63) Continuation of application No. 08/164,879, filed on Dec. 9, 1993, now Pat. No. 6,251,952, which is a continuation-in-part of application No. 07/645,175, filed on Jan. 24, 1991, now abandoned.

(51) Int. Cl.$^7$ .................................................. A61K 31/095
(52) U.S. Cl. ............................................ 514/706; 514/912
(58) Field of Search ..................... 514/706, 912

(56) References Cited

U.S. PATENT DOCUMENTS

| | | | |
|---|---|---|---|
| 2,235,453 | 3/1941 | Kirmes ................................ | 91/67.2 |
| 2,681,252 | 6/1954 | Tuttle .................................. | 299/95 |
| 3,207,441 | 9/1965 | Schreiber ............................ | 239/47 |
| 3,361,306 | 1/1968 | Grim .................................. | 222/402 |
| 3,559,851 | 2/1971 | Steiman ............................. | 222/402 |
| 3,679,133 | 7/1972 | Sekiguchi et al. .................. | 239/34 |
| 4,010,875 | 3/1977 | Babiol ................................ | 222/517 |
| 4,017,030 | 4/1977 | Coplan et al. ...................... | 239/44 |
| 4,539,450 | 9/1985 | Lorenz et al. ...................... | 200/148 |
| 4,680,283 | 7/1987 | Veber et al. ........................ | 530/332 |
| 4,728,037 | 3/1988 | Mainhardt .......................... | 239/154 |
| 4,944,429 | 7/1990 | Bishop .............................. | 222/153 |
| 5,002,228 | 3/1991 | Su ...................................... | 239/333 |

FOREIGN PATENT DOCUMENTS

| | | |
|---|---|---|
| 504353 | 4/1939 | (GB) . |
| 49-35198 | 8/1972 | (JP) . |
| 63-280015 | 11/1988 | (JP) . |

OTHER PUBLICATIONS

M. H. Brodnitz and J. V. Pascale, Thorpropanal S–Oxide: A Lachrymatory Factor in Onions, *J. Agr. Food Chem.*, vol. 19, No. 2, 1971 pp. 269–272.

M. Nagarajan, H. Schecter, Structure and Origin of the Onion Lachrymatory Factor. A Microwave Study, *Journal of the American Chemical Society*, vol. 101 and 102, No. 8 and No. 7, Apr. 11, 1979 and Mar. 26, 1980 pp. 2200–2201, and pp. 2490–2491.

K.L. Bajaj, Chemical Evaluation of some Important Varieties of Onion, *Vegetable Crops, Lanscaping and Floriculture* Punjab Agricultural Univ., Ludhiana– 1410045, India, Qualitas Plantarum 30 (2) pages 117–122.

E. Block, et al., The Lachrymatory Factor of the Onion: an NMR Study, *Tetrahedron Letters* vol. 21, 1980, pp. 1277–1280.

K.L. Bajaj et al., The Lachrymatory Factor and Other Chemical Constituents of Some Varieties of Onion, *Journal of Plant Foods* vol. 3, 1979 pp. 199–203.

*Primary Examiner*—Zohreh Fay
(74) *Attorney, Agent, or Firm*—Pennie & Edmonds LLP

(57) ABSTRACT

Substances, methods and devices for moisturizing the eye by stimulation of the lachrymatory glands to cause generation of tears.

22 Claims, 3 Drawing Sheets

PRODUCT FOR MOISTURIZING AN EYE

RELATED APPLICATIONS

This is a Continuation of patent application Ser. No. 08/164,879, filed Dec. 9, 1993, now U.S. Pat. No. 6,251,952, which is a Continuation-in-part of patent application Ser. No. 07/645,175, filed Jan. 24, 1991, now abandoned.

BACKGROUND OF THE INVENTION

This invention relates to methods, apparatus and substances for moisturizing the eye and particularly to moisturizing the eye with natural tears, i.e., by inducing natural tear production rather than introducing artificial tears.

Many people suffer from what is commonly known as "dry eye". The condition arises from lack of sufficient tear production and results in a variety of symptoms such as burning, itching and undue sensitivity to smoke. The condition is more common in older adults inasmuch as a gradual lessening of tear production is a natural concomitant of the aging process. However, younger persons also suffer dry eye as a pathological disorder and the problem is particularly acute with the wearers of contact lenses. In this case, tear production may be entirely adequate for normal purposes but insufficient to provide adequate wetting and lubrication to permit wearing such lenses in comfort.

As any wearer of contact lenses knows, the low humidity of the average home or office in winter, windy days, and other ambient climatological conditions greatly aggravate the situation and often times precludes wearing contact lenses. With prolonged wear under drying conditions, the eye sometimes generates mucous which coats the lenses to the point that they can become opaque. If this occurs while the wearer is reading, say, a research paper before a learned society or making a presentation at a business meeting, it can be embarrassing; while driving, dangerous.

With more than discomfort involved, it is important that the eyes be quickly, easily, and effectively moisturized and there is a need to do this without embarrassment in public places and social situations.

THE PRIOR ART

At the present time numerous eye moisturizing products are available ranging from simple artificial tears to lens clearing and lubricating solutions and additives calculated to "get the red out".

While these products vary widely in effectiveness, cost and the claims made for them, they have one thing in common: insofar as is known, all are liquids intended for macroscopic introduction into the eye in the form of drops and are packaged either in plastic squeeze-bottle droplet dispensers or glass containers having caps fitted with an eye dropper. They are intended to be administered by tilting back one's head, putting the dropper nozzle over and in proximity to the eye (being careful to observe the label warning not to touch the tip lest the contents of the dispenser become contaminated), and allow a drop or two to fall into one eye at a time.

Another method of administration of liquid drops involves pulling down the lower eyelid to form a pocket and placing the drops into the pocket.

With practice, some users become so proficient with one or the other technique that they can get a high percentage of the drops dispensed to fall into the eye. Near misses can be dealt with if tissues are handy and, if not, the drops roll harmlessly down the cheeks, the only occasional casualty being smeared mascara unless of course one is foolish enough to attempt the administration while driving!

From the foregoing it will be noted that a well-equipped wearer of contact lenses should carry: a lens case (to store the lenses in the event that dryness forces their removal); a pair of corrective spectacles to substitute for the "contacts"; a bottle of eye drops; and a supply of tissues.

Those persons who do not wear or aspire to wear contact lens but have dry eye suffer only slightly fewer vexations, viz., they are not burdened with the contact wearers paraphernalia.

With the foregoing state of the art in view, it is the object of this invention to overcome or at least mitigate the problems of the prior art as outlined above.

A further object is the provision of methods and means for moisturizing the eye without introducing moisturizing liquid into the eye.

Another object is to provide methods and means for inducing "dry eyes" to generate natural tear in situ. A still further object is to provide means for moisturizing the eye which can be employed discretely and without attracting notice in public places.

BRIEF DESCRIPTION OF THE INVENTION

To the fulfillment of these and other objects, the invention contemplates a method for moisturizing the eye by the microscopic introduction into the eye in gaseous or vapor form, a substance causing the generation of tears by the lachrymatory glands.

The substance is a lachrymatory agent vaporizable at room temperature diluted to a concentration which causes tearing of the eye without untoward smarting or irritation.

The invention further contemplates a device for moisturizing the eye comprising a container having an opening and a closure member normally closing the opening. Means are provided for opening the closure member and a lachrymatory agent as described above is disposed in the container.

A kit comprising an amount of lachrymatory agent and means for dispensing an effective amount of said lachrymatory agent to cause tears.

DESCRIPTION OF PREFERRED EMBODIMENTS

Figure 1:
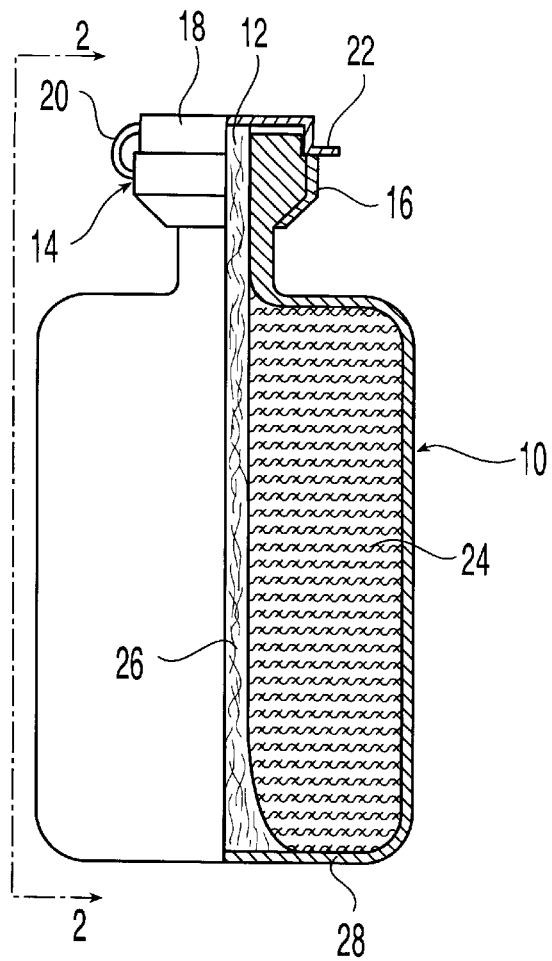
FIG. 1 is a side elevation, partly in section on the vertical center line, of a device for moisturizing the eye embodying the invention.
Figure 2:
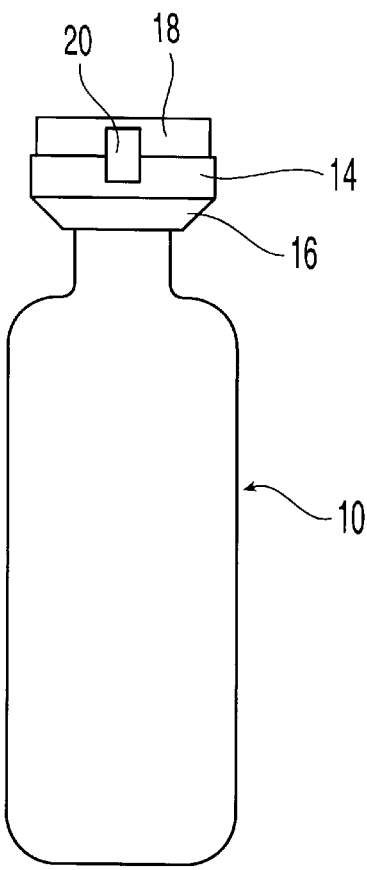
FIG. 2 is an elevational view taken on line 2—2 of FIG. 1, looking in the direction of the arrows.

It has been determined that the smarting and tearing effect associated with peeling onions is caused by propanethial-s-oxide ('PSO") and related compounds naturally occurring in onions. (See "PROPANETHIAL-S-OXIDE", Chemical Abstracts Registry #3215729-2). The compounds are quite volatile, vaporizing at room temperature. These compounds, the most significant of which is propanethial-s-oxide, and other compounds having similar chemical and physical properties, viz., lachrymatory activity and volatility, can be diluted and utilized to stimulate tearing to combat pathogenic and benign dry eye conditions.

The method of moisturizing the eye contemplated by the invention consists of the fundamental step of introducing into the eye, in vapor, gaseous or otherwise microscopic form, a lachrymatory compound(s) naturally occurring in onions. For the purposes of this specification the term microscopic is defined to encompass misting, vaporous or gaseous methods of introducing lachrymatory agents into the eye. The lachrymatory compounds may be appropriately diluted to a concentration that is suitable to the individual using it. The concentration must be determined empirically as the strength of the compounds in onions varies widely with the variety of onion used, growing conditions, etc. The desideratum is a concentration which produces sufficient tearing without undue burning or smarting of the eye.

The preferred composition comprises an amount of PSO and related compounds to produce tears after a short exposure time. The purity of the compounds will have a direct effect on the production of tears. It is preferred to use pure PSO and related compounds, although the PSO and related compounds maybe diluted to promote the volatility of the PSO. Common pharmaceuticals adjuvants may also be added to the compositions to produce the desired composition. Said common pharmaceutical adjuvants can be found in Remingtons Pharmaceutical Sciences, fifth edition, by Mack Publishing Company, which publication is herein specifically incorporated by reference. The desired composition may be any that is known to those skilled in the art and can be based on, for example, an aerosol composition employing a propellant, or a volatile composition using volatility enhancers, such as, for instance, ethyl alcohol.

A device for introducing the lachrymatory agent will now be described with reference to the drawings and, first, to FIGS. 1 to 4 showing a container 10 having an opening 12 at its upper end. A cap assembly 14 includes a mounting band 16 tightly encircling opening 12 and a captive closure member 18 secured to the band by a hinge 20 consisting of a strip of flexible plastic or other material.

Closure member 18 is of the type often referred to as a "snap-cap" and is closed by means of downward finger pressure applied on its top surface, preferably at a point diametrically opposite hinge 20. In this condition, the cap closes opening 12.

A radially projecting tab 22 on cap 18 facilitates opening the container which is accomplished by upward pressure on the tab. Thus opening can be accomplished with a single finger, usually the thumb, by pushing tab 22 upwardly; when in the open position, shown in FIG. 4, the cap is held captive by hinge 20.

Figure 3:
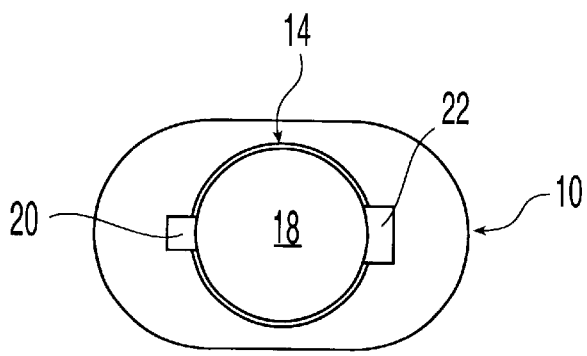
FIG. 3 is a top plan view of FIGS. 1 and 2.
Figure 4:
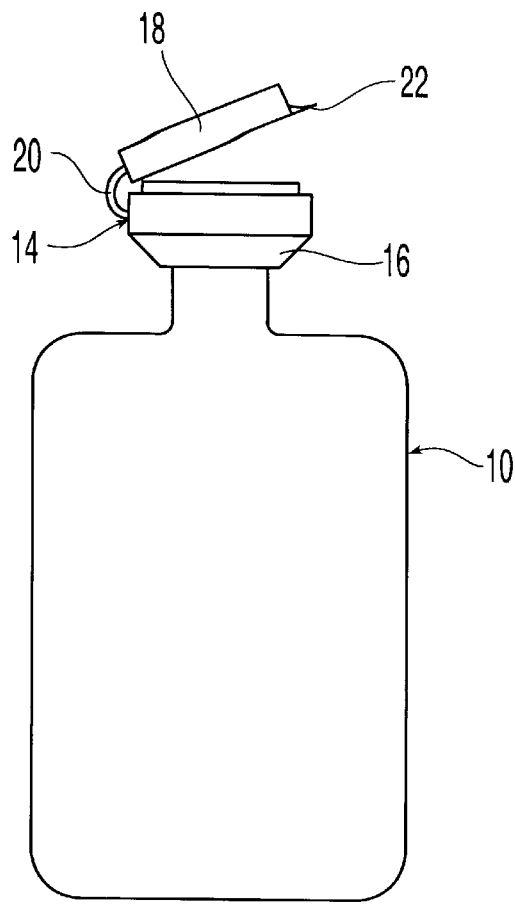
FIG. 4 is an elevational view of the structure in FIG. 1 with parts in an alternate position.

Container 10 has a generally ovate cross-section as appears in FIG. 3, lending itself to a comfortable fit in the user's palm and permitting easy removal and replacement of the cap.

Container 10 is filled to the desired level with the lachrymatory agent; preferably the agent is absorbed in a matrix of suitable absorbent material such as cotton shown at 24 in FIG. 1. Whether or not a matrix is used, it is preferred that a wick 26 be disposed in the container extending from a point at or near its bottom 28 and extending to opening 12, terminating flush with the face of the opening.

To moisturize the eye, the user simply positions the opening of the container close to his eye, opening the cap before or after doing so. (There is no need to tilt the head back.) The vapor from the container enters the eye and almost immediately stimulates tear production by the lachrymatory glands. After a few moments, i.e., when the desired effect is obtained, the process is repeated with the other eye. Then the cap is replaced and the container restored to purse or pocket.

Figure 5:
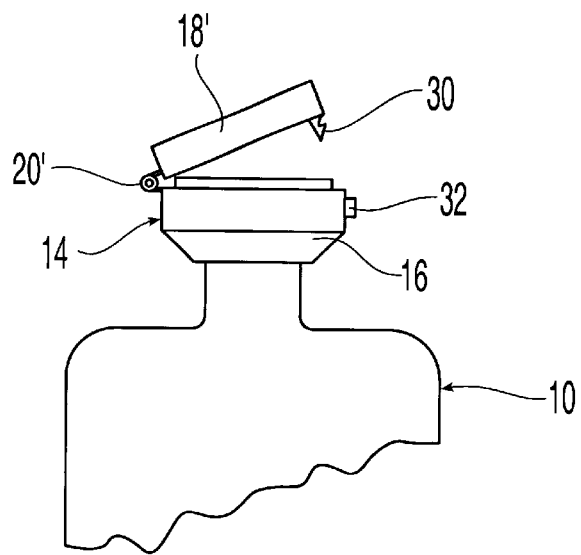
FIGS. 5, 6 and 7 are views similar to FIG. 4 showing modified embodiments of the invention.

An alternative form of the moisturizer is shown in FIG. 5 wherein the cap assembly 14' is modified as compared to FIGS. 1–4 by the substitution of a spring hinge 20' for hinge 20.

Spring hinge 20' resiliently biases cap 18 toward its open position and a latch is provided diametrically opposite the hinge. When engaged, the latch maintains the cap in closed position against the bias effect of the spring. A latch release button 32, when pressed, causes the cap to snap open; it is closed by applying downward pressure on the top surface of the cap in the same manner as the previously described embodiment. The use of the FIG. 5 moisturizer is entirely analogous to and will be readily apparent from the above-described use of the device in FIGS. 1–4.

Figure 6:
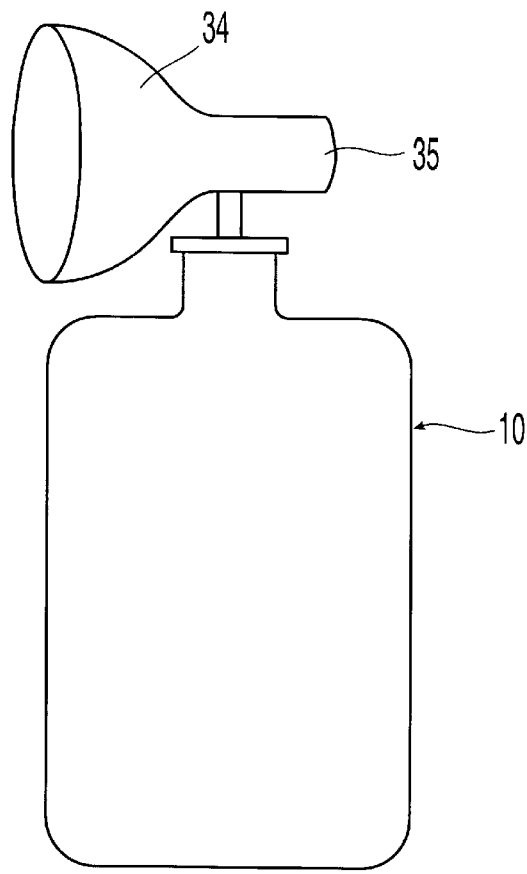
Figure 7:
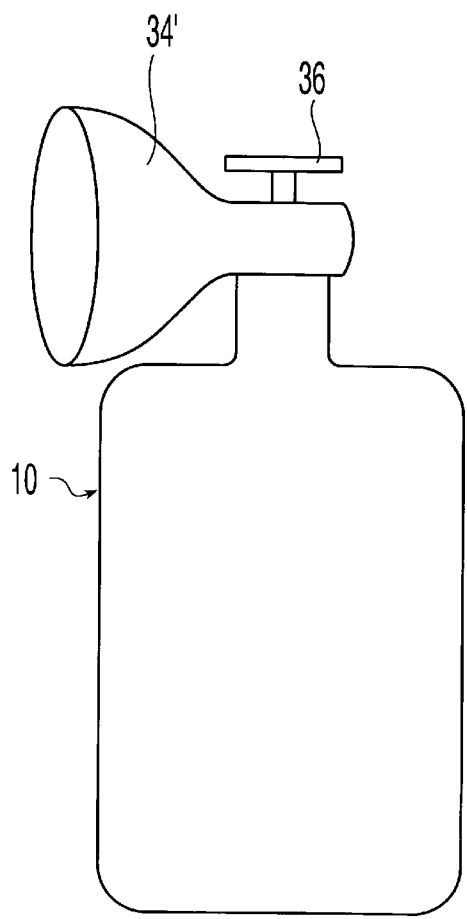

FIGS. 6 and 7 show further embodiments of the invention each including a preferably soft plastic cup-shaped member 34 and 34', respectively, mounted on a container 10. Members 34, 34' are configured and dimensioned to fit over the eye and are, in use, selectively placed in flow communication with the interior of the container so as to guide and confine vapor issuing there from to the ocular region.

The FIG. 6 embodiment is a non-aerosol, pump-type dispenser which ejects a measured quantity of the contents of the container 10 each time the member 34 is depressed as by finger pressure on the flat 35 provided thereon for the purpose.

FIG. 7 illustrates an aerosol-type unit in which the contents of container 10 are under pressure and a metered quantity ejected into member 341 when a valve actuation button 36 is pressed. It will be understood that the construction and operation of the pump and aerosol dispensing devices per se are well known. However the substance issuing from the device is not an aerosol or spray but a vapor.

The use of the devices shown in FIGS. 6 and 7 is completely analogous to that of the FIG. 1–4 embodiment of the invention already described except, of course, that the cup-shaped member 34, 34' is placed over the eye before dispensing the lachymatory vapor.

The use of a kit comprising means for dispensing lachrymatory agent and the lachrymatory agent itself is also within the scope of this invention. A preferred kit would use an apparatus for dispensing said lachrymatory agent as described above containing a lasting supply of lachrymatory agent. Such kit would be packaged in a shrink wrapped package or a hard plastic protection pack. The packaging material used in the kit can be any material known to those skilled in the art. Such materials can include cardboard, plastic and any combination of the two, for example.

From the foregoing description of exemplary embodiments, it will be seen that the objects of the invention are achieved, enabling moisturization of the eyes discretely and effectively, using a single hand, without tilting the head or possibility of misapplication of liquid drops. The scope of this invention is intended to include all such modifications that would be obvious to one of ordinary skill in the art.

What is claimed is:

1. A product for combating a pathogenic, benign, dry or irritated eye condition comprising:
   a container having a normally closed opening and an interior compartment, the interior compartment holding an amount of propanethial-s-oxide sufficient to provide a plurality of individual dosages of sufficient strength to induce tearing in a mammalian eye; and a closure member cooperating with said opening and being selectively movable between a normally closed position, and an open position for releasing a microscopic quantity of propanethial-s-oxide through said opening.

2. The product according to claim 1, wherein the container is a bottle and the closure member is a cap suitable for covering the bottle.

3. The product according to claim 1, wherein the closure member is spring-biased towards the open position and the product includes a releasable latch for normally maintaining the closure member in the closed position.

4. The product according to claim 1, wherein the closure member is secured to the container by a flexible hinge.

5. The product according to claim 4, wherein the closure member is provided with a radially projecting tab which, upon upward pressure, moves the closure member from the normally closed position to the open position.

6. The product according to claim 1, wherein the closure member comprises a non-aerosol pump-type dispenser which ejects a measured quantity of propanethial-s-oxide each time the dispenser is depressed.

7. The product according to claim 1, wherein the closure member comprises a valve actuated by a button and propanethial-s-oxide within the interior compartment is under pressure.

8. The product according to claim 1, further comprising a matrix material situated in the interior compartment, wherein the propanethial-s-oxide is absorbed in said matrix material.

9. The product according to claim 8, wherein the matrix material is cotton.

10. The product according to claim 8, further comprising a wick situated in the interior compartment, the wick extending from a point at or near a bottom of the interior compartment, to said container opening.

11. The product according to claim 1, further comprising a wick situated in the interior compartment, the wick extending from a point at or near a bottom of the container, to its opening.

12. The product according to claim 1, further comprising a cup-shaped member attached to the product and configured and dimensioned to fit over an eye.

13. The product according to claim 1, placed in a package.

14. The product according to claim 1, wherein the package comprises plastic, cardboard or a combination of plastic and cardboard.

15. A product for combating a pathogenic, benign, dry or irritated eye condition comprising:

a container having a normally closed opening and an interior compartment, the interior compartment holding an amount of a lachrymatory agent sufficient to provide a plurality of individual dosages of sufficient strength to induce tearing in a mammalian eye; and a closure member cooperating with said opening and being selectively movable between a normally closed position, and an open position for releasing a microscopic quantity of said lachrymatory agent through said opening, and a package comprising plastic, cardboard or a combination of plastic and cardboard, said package holding said container and said closure member.

16. The product according to claim 15, wherein the lachrymatory agent comprises propanethial-s-oxide.

17. The product according to claim 16, wherein the closure member is spring-biased towards the open position and the product includes a releasable latch for normally maintaining the closure member in the closed position.

18. The product according to claim 16, wherein the closure member is secured to the container by a flexible hinge.

19. The product according to claim 16, wherein the closure member comprises a non-aerosol pump-type dispenser which ejects a measured quantity of said lachrymatory agent, each time the dispenser is depressed.

20. The product according to claim 16, wherein the closure member comprises a valve actuated by a button and the lachrymatory agent within the interior compartment is under pressure.

21. The product according to claim 16, further comprising a matrix material situated in the interior compartment, wherein the lachrymatory agent is absorbed in said matrix material.

22. A product for combating a pathogenic, benign, dry or irritated eye condition comprising:

a container having a normally closed opening and an interior compartment, the interior compartment holding an amount of a lachrymatory agent sufficient to provide a plurality of individual dosages of sufficient strength to induce tearing in a mammalian eye; and a closure member cooperating with said opening and being selectively movable between a normally closed position, and an open position for releasing a microscopic quantity of said lachrymatory agent through said opening.

* * * * *